(12) United States Patent
Patil et al.

(10) Patent No.: US 11,744,543 B2
(45) Date of Patent: *Sep. 5, 2023

(54) EVALUATION OF CARDIAC INFARCTION BY REAL TIME ULTRASONIC STRAIN IMAGING

(71) Applicant: KONINKLIJKE PHILIPS N.V., Eindhoven (NL)

(72) Inventors: Abhay Vijay Patil, Andover, MA (US); Atul Ingle, Andover, MA (US); Karl Erhard Thiele, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 115 days.

This patent is subject to a terminal disclaimer.

(21) Appl. No.: 17/378,978

(22) Filed: Jul. 19, 2021

(65) Prior Publication Data

US 2022/0022843 A1    Jan. 27, 2022

Related U.S. Application Data

(63) Continuation of application No. 15/545,748, filed as application No. PCT/IB2016/050308 on Jan. 22, 2016, now Pat. No. 11,109,832.

(Continued)

(51) Int. Cl.
*A61B 8/08*    (2006.01)
*A61B 8/00*    (2006.01)

(52) U.S. Cl.
CPC .......... *A61B 8/0883* (2013.01); *A61B 8/485* (2013.01); *A61B 8/5246* (2013.01); *A61B 8/543* (2013.01); *A61B 8/461* (2013.01)

(58) Field of Classification Search
CPC ..... A61B 8/0883; A61B 8/485; A61B 8/5246; A61B 8/543; A61B 8/461
See application file for complete search history.

(56) References Cited

U.S. PATENT DOCUMENTS 6,749,571 B2   6/2004   Varghese et al.
6,994,673 B2   2/2006   Lysyansky
(Continued)

FOREIGN PATENT DOCUMENTS

JP    2006141451 A    6/2006

OTHER PUBLICATIONS

Ma et al: "Lagrangian Displacement Tracking Using a Polar Grid Between Endocardial and Epicardial Contours for Cardiac Strain Imaging"; Medical Pysics 39.4 (2012):1779-1792.

(Continued)

*Primary Examiner* — Sean D Mattson

(57) ABSTRACT

Real time strain imaging is provided by acquiring a sequence of cardiac image frames and estimating tissue displacement in the myocardium over a heart cycle. The displacements are used to calculate strain over the myocardium and a color map is formed of the strain values. During the next heart cycle the color map is warped to fit the myocardium in each image frame and the warped color map is displayed as a color overlay over the myocardium of each image of the new heart cycle as they are displayed in real time. A new color map is also produced over the new heart cycle for use with the following heart cycle. An ultrasound system which performs real time strain imaging is also described.

14 Claims, 5 Drawing Sheets

Related U.S. Application Data

(60) Provisional application No. 62/109,209, filed on Jan. 29, 2015.

(56) References Cited

U.S. PATENT DOCUMENTS

| | | |
|---|---|---|
| 8,150,128 B2 | 4/2012 | Konofagou et al. |
| 11,109,832 B2 * | 9/2021 | Patil .................. A61B 8/543 |
| 2003/0083578 A1 | 5/2003 | Abe et al. |
| 2004/0059224 A1 | 3/2004 | Varghese |
| 2005/0288589 A1 | 12/2005 | Houle et al. |
| 2008/0285819 A1 * | 11/2008 | Konofagou ............ A61B 8/485 382/128 |
| 2009/0318803 A1 | 12/2009 | Abe et al. |
| 2010/0004540 A1 | 1/2010 | Thiele |
| 2012/0078097 A1 | 3/2012 | Wang et al. |
| 2013/0253319 A1 | 9/2013 | Hamilton |
| 2013/0286023 A1 | 10/2013 | Friedman et al. |
| 2014/0112544 A1 | 4/2014 | Yu |

OTHER PUBLICATIONS

Luo et al.: "Detection of Murine Infarcts Using Myocardial Elastography at Both High Temporal and Spatial Resolution"; Conference Proceedings of the 28TH IEEE EMBS Annual International Conference, Aug.-Sep. 2006, pp. 1552-1555.

\* cited by examiner

EVALUATION OF CARDIAC INFARCTION BY REAL TIME ULTRASONIC STRAIN IMAGING

This application is a continuation of U.S. patent application Ser. No. 15/545,748 entitled "EVALUATION OF CARDIAC INFARCTION BY REAL TIME ULTRASONIC STRAIN IMAGING", filed on Jul. 24, 2017, which in turn is the U.S. National Phase application under 35 U.S.C. § 371 of International Application No. PCT/IB2016/050308, filed on Jan. 22, 2016, which claims the benefit of U.S. Provisional Application Ser. No. 62/109,209, filed on Jan. 29, 2015. These applications are hereby incorporated by reference herein.

This invention relates to ultrasonic diagnostic imaging systems and, in particular, to the use of ultrasonic strain imaging to evaluate ischemic areas of the heart which have suffered an infarct.

One of the uses of cardiology ultrasound is to evaluate the heart of a patient who has suffered an infarct. It would be desirable, for instance, to be able to image the coronary arteries to look for blockages that may have caused an ischemic event. Ultrasound, however, is generally not capable of directly visualizing the coronary arteries due their motion, location outside the heart, proximity to the lungs, and other characteristics. Thus, arterial functions are indirectly diagnosed with ultrasound by assessing myocardial wall motion. An abnormal or asynchronous wall motion suggests reduced arterial flow, probably due an occlusion of a coronary artery by an arterial plaque or blood clot. Abnormal functioning of the myocardium due to an occlusion can be diagnosed by visualizing the contractility of the myocardium. Contractility can be assessed by calculating myocardial mural strains throughout the heart muscle as the heart contracts, looking for areas where the deformation during contraction is minimal or erratic. Unfortunately, most current approaches lack the resolution to image local strains and are not real-time. Existing strain imaging can only measure global strains (longitudinal, circumferential and radial) over the heart cycle. While useful, they cannot be used to localize and reliably visualize an infarct or demarcate an ischemic region. These applications lack the sensitivity required to diagnose local heart functions. Furthermore, since strain is determined by tracking myocardial motion over the full heart cycle or at least its contraction phase, only one strain image can be produced for a heart cycle. These images are viewed statically and not as real time motional images. Accordingly it is desirable to be able to determine cardiac contractility characteristics with high resolution and to be able to view them in real time cardiac images.

In some aspects, the present invention includes ultrasound systems, such as an ultrasonic diagnostic imaging system for real time strain imaging that includes an ultrasound imaging probe having an array transducer which acquires ultrasound echo signals, an image processor, coupled to the imaging probe, which produces a first sequence of image frames in real time, a strain calculator coupled to the image processor which processes image frame data to estimate strain during the image frame sequence, a color mapper which produces a color map from strain values, a color map warper that is responsive to the color map and a new sequence of image frames and configured to warp the color map to an image frame of the new sequence to generate a warped color map, and a display which displays an image frame in combination with the warped color map.

In certain aspects, the present invention can include an ultrasound imaging system having instructions thereon, which when executed, cause the system to acquire ultrasound echo signals using an ultrasound imaging probe having an array transducer, produce a first sequence of image frames in real time, process image frame data of the image frames to estimate strain during the image frame sequence, produce a color map based at least in-part on the strain values, warp or fit the color map to an image frame of a new sequence of images to generate a warped color map, and display an image frame in combination with the warped color map.

In some aspects, the present invention includes methods of ultrasound imaging, such as a method of producing real time ultrasonic strain images, which includes acquiring frames of echo image data, estimating tissue displacements between acquired frames from the echo image data, calculating strain values from the displacements, forming a color map of the strain values, acquiring additional frames of echo image data, warping the color map to the additional frames, and displaying the additional frames in combination with warped color maps.

In the drawings:

FIG. 1 is a block diagram of an ultrasound system constructed in accordance with the principles of the present invention.

FIG. 2A, FIG. 2B, FIG. 2C, and FIG. 2D collectively illustrate the motion of points in the myocardium during the contraction of the heart.

Figure 6:
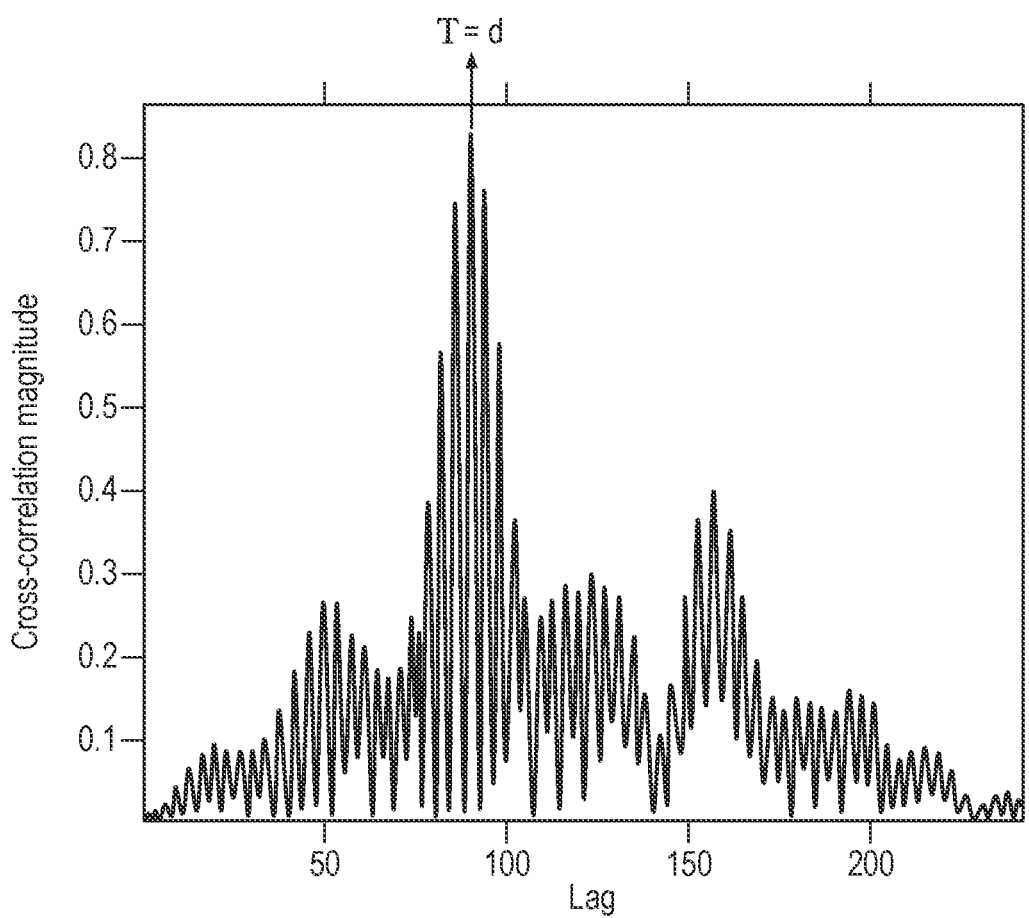

FIG. 6 graphically illustrates a typical cross-correlation distribution of speckle from a moving heart in an embodiment of the present invention.

In accordance with the principles of the present invention, an ultrasonic diagnostic imaging system is described which is able to image the heart at a high frame rate and calculate strain over localized areas of the myocardium. For each pixel on the image, a strain parameter is determined which is representative of the local strain, and these pixel values are then mapped spatially to the anatomical image. The strain map is then fitted to the first image of the next heart cycle and displayed as a parametric color overlay over the image frames of the next cycle of heart images. As the images change with the contraction and relaxation of the myocardium, the color overlay is warped to continually fit over each cardiac image. The user is thus given a real time display of the heart, its spatial strain variation, and corresponding contractility characteristics.

In some aspects, the present invention provides ultrasonic diagnostic imaging systems for real time strain imaging. The ultrasound systems can include a variety of components, such as an ultrasound imaging probe. The probe can include an array transducer which acquires ultrasound echo signals. The systems can include an image processor. The image processor can be coupled to the imaging probe and configured to produce a first sequence of image frames in real time. The systems can include a strain calculator coupled to the image processor. The strain calculator can be configured to process image frame data to estimate strain during the image frame sequence. The systems can include a color mapper. The systems can be configured to include processors, memory, and other structures that can be programmed to serve as a color mapper. The color mapper can be configured to produce a color map based on the strain values. The systems can include a color map warper. The systems can include a color mapper. The systems can be configured to include processors, memory, and other structures that can programmed to serve as a color map warper. The color map warper can be responsive to the color map and a new sequence of image frames and configured to warp the color map to an image frame of the new sequence, thereby generating a warped color map. The systems can also include a display which displays an image frame in combination with the warped color map.

In some embodiments, the image frames can include cardiac image frames. The first sequence of image frames can be acquired during a first heart cycle, and a new sequence of image frames can be acquired during a subsequent heart cycle. The systems can include a frame memory, coupled to the image processor, which stores sequences of image frames.

In certain embodiments, the systems can include a displacement estimator. The systems can include a color mapper. The systems can be configured to include processors, memory, and other structures that can be programmed to serve as a displacement estimator and the color mapper. The displacement estimator can be responsive to a sequence of image frames can configured to estimate tissue displacements over the image frame sequence. The displacement estimator can include a displacement cross-correlator which estimates displacements by cross-correlating echo data, and a displacement integrator which performs Lagrangian integrated displacement values.

In some embodiments, the systems can include a speckle tracker which identifies tissue displacements. The systems can include a color mapper. The systems can be configured to include processors, memory, and other structures that can be programmed to operate as the speckle tracker and the color mapper. In certain embodiments, the systems can be coupled to an ECG sensor, which senses a patient ECG waveform. The systems can further include a beamformer, coupled to the array transducer, which operates to acquire image frame sequences in relation to the ECG waveform.

Figure 1:
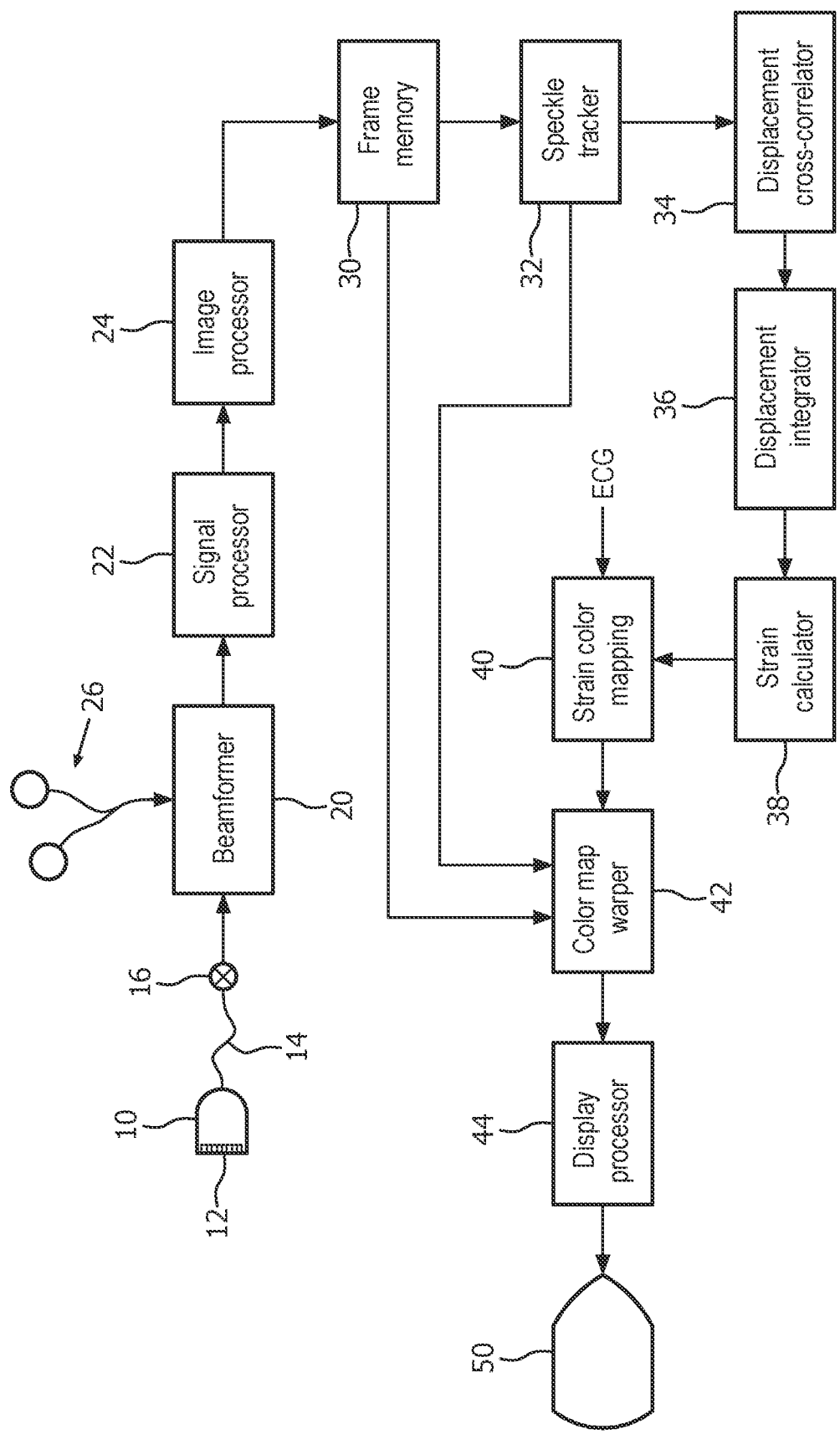

Referring first to FIG. 1, an ultrasound system constructed in accordance with the principles of the present invention is shown in block diagram form. A probe 10 has a transducer array of elements 12 which scans the region of the body in front of the array. The array may be a one-dimensional or a two-dimensional array for 2D or 3D scanning. Typically in cardiology the array transducer is operated as a phased array. The probe is operated by a beamformer 20 which controls the timing of transmit pulses and processes received echo signals. The probe 10 is coupled to the mainframe ultrasound system by a probe cable 14 and a transmit/receive switch 16 which protects sensitive electronics of the beamformer during high voltage transmission. The beamformer delays and combines signals received from the transducer elements to form coherent echo signals from points in the image field. The echo signals are coupled to a signal processor 22 which enhances the signals as by filtering and produces detected echo signals. The processed echo signals are then formed into a spatial image of the desired format by an image processor 24. Successively produced image frames are stored in a frame memory 30.

Figure 5:
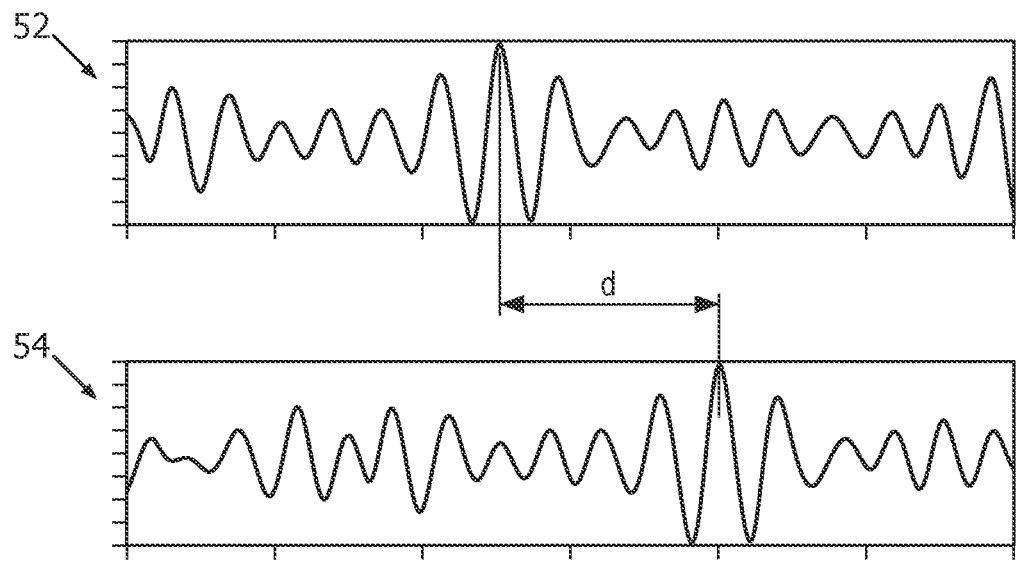
FIG. 5 illustrates cross-correlation functions of the echo data of consecutive images of the heart.

Since it is not possible to determine stress in the myocardium by ultrasound directly, the force applied by the heart muscle, the effect of such force is estimated by measuring strain, the deformation of the heart resulting from contractile stress. The strain measurement process begins by tracking the motion of the myocardium as it contracts. Since ultrasound produces coherent signals, it exhibits a phenomenon known as speckle. So long as the probe remains stationary, the speckle pattern will persist from one image frame to the next. The detailed speckle pattern is tracked by a speckle tracker 32, which thereby follows small regions of myocardial tissue by following the change in position of their speckle pattern from one image frame to the next. Since the echo signal intensity variation resulting from speckle is at a very low level and thus susceptible to being masked by noise, the system of FIG. 1 estimates displacements of the speckle pattern from one image to the next by cross-correlation. The echoes of consecutive image frames are cross-correlated by a displacement cross-correlator 34 to locate the peak of the cross-correlation function. A typical cross-correlation function is shown in FIG. 6. FIG. 5 illustrates one cross-correlation function 52 from the cross-correlation of first and second consecutive image frames, and a second cross-correlation function 54 from the cross-correlation of the second and the next consecutive image frames. As seen there is a lag d between the peaks of the two functions. This lag d is the displacement of the tissue in the image sequence from one frame to the next. Because this lag signal is susceptible to noise, the displacements over a plurality of consecutive frames are integrated by a displacement integrator 36. Preferably Lagrangian integration is used to produce a single value for each point in the myocardium which is representative of the displacements over the plurality of consecutive frames. Because the heart motion is cyclic and hence it will return to its original starting point each heart cycle (the heart in frame 1 is in the same position as it is in the last frame N), it is possible to get two independent estimates for the displacement over the contractile and relaxation phases. For example, instantaneous displacements are integrated forward in time from frames 1 to M (denoted by $I_{1-M}$) and reverse in time from frame N to M (denoted by $I_{M-N}$). Note that frame M corresponds to end systole; this is the phase of the heart cycle at which the strains should be at a maximum. The integrated displacements are then averaged to create a Lagrangian integrated composite displacement map: $I_G = (I_{1-M} + I_{M-N})/2$. The integrated displacements are then used by a strain calculator 38 to produce spatial derivatives which are spatial strain values for each pixel location. A weighted combination of nominal and shear strain values is used to create a parametric image. One example of such combination is: $(0.5E_{yy} + 0.25E_{xy} + 0.25E_{xx})$, where $E_{xx}$ is the strain perpendicular to an A-line, $E_{yy}$ is strain along the A-line and $E_{xy}$ is the shear strain extracted from axial displacements. This is a measure of rotation. These strain values are then mapped as color values in a two-dimensional or three-dimensional color map by strain color mapping 40. The color map spatially corresponds to the myocardium as it appears in the image frames over which the strain values were calculated. The color map could be displayed as a static color map of strain for the heart cycle over which the strain values were calculated.

In accordance with the principles of the present invention, the strain color map is stored in the strain color mapping processor 40 and frames are acquired over a subsequent heart cycle. Preferably frames of each heart cycle are acquired at known phases of the heart cycle in relation to the R-wave of the heart's ECG signal. As is well known, physiological electrodes 26 are attached to the patient's body during scanning for the production of an ECG waveform and image frame acquisition timing can thereby be based upon the timing of the R-wave of the ECG signal.

When the R-wave of the subsequent heart signal is produced, it triggers the strain color mapping processor 40 to couple the color map to a color map warper 42. The color map warper receives an image frame produced during the new heart cycle and may optionally also receive spatial information on the tracked speckle in the new image from the speckle tracker 32. The color map warper then warps or fits the color map from the previous heart cycle to the cardiac image of the new heart cycle. With the color map thus spatially aligned to the myocardium in the new image frame, the warped color map and the new image frame are coupled to the display processor, where the color map is applied as a color overlay over the image frame. The new image frame and its color overlay of the warped color map are then displayed on a display 50.

As successive image frames of the new heart cycle are received they are coupled to the color map warper 42 and the color map produced during the previous heart cycle is warped or fit to the myocardium in each image. The color map of the myocardial strain is thereby fit within the boundary of the myocardium in each image of the new heart cycle. Each warped color map is then displayed as a color overlay superimposed over each successive cardiac image frame of the new heart cycle. The real time display of the image frames of the new heart cycle thus includes the fitted strain color overlay which thereby displays a dynamic real time image sequence of the strain characteristics of the myocardium.

Optionally, the tracked speckle values of each new image frame of the new heart cycle can be used by the color map warper 42 to fit the strain values of the color map to corresponding speckle locations in each new image frame. Rather than warping the color map as a whole, the strain values of the color map are continually repositioned to match with their changing corresponding speckle locations in each new image frame.

At the same time that this display methodology is ongoing, elements 32-40 of the ultrasound system are calculating strain values over the new heart cycle so that a new color map is produced for the new heart cycle. The new color map is then used as a new warped color overlay for the following cardiac cycle.

Figure 2A:
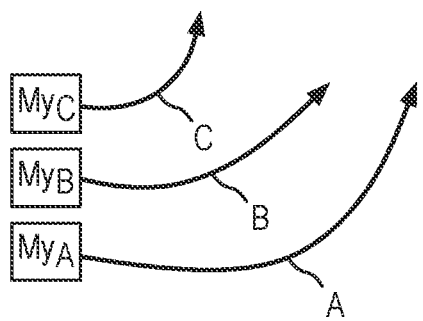
Figure 2B:
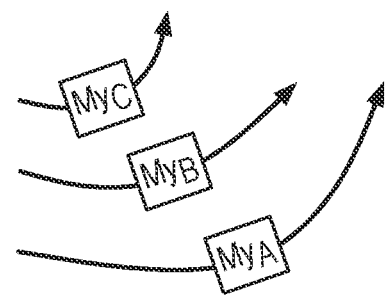
Figure 2C:
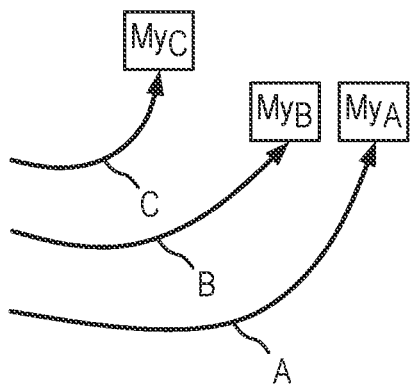
Figure 2D:
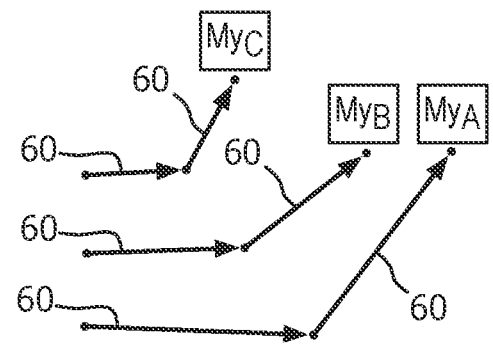
Figure 3:
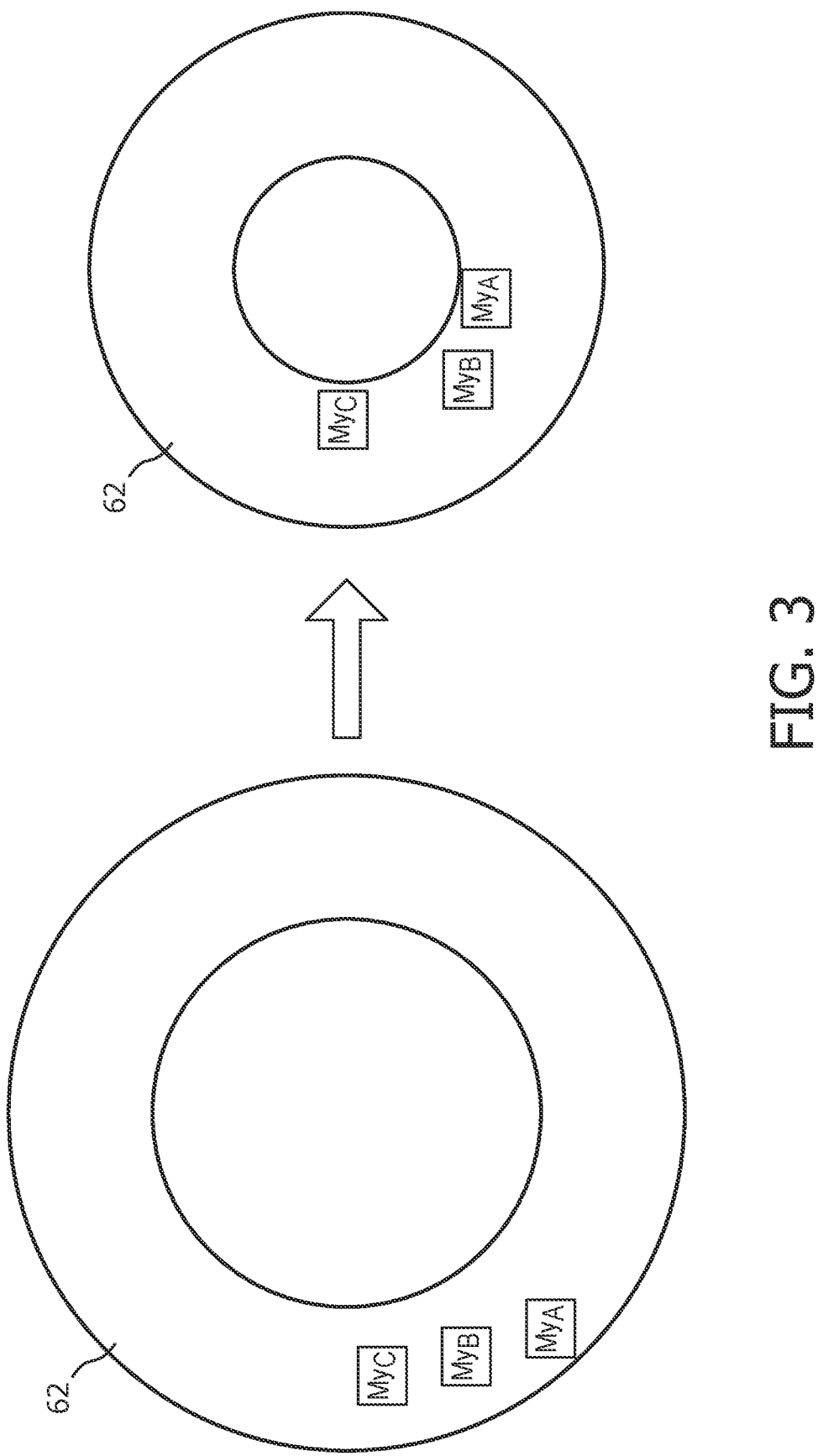
FIG. 3 illustrates motion of points in the myocardium when observed in a short axis view of the heart.

FIGS. 2A-2D illustrate how individual points of the myocardium can move during a contraction of the heart and how this movement manifests itself in ultrasound images. FIG. 2A shows three points in the myocardium, $My_A$, $My_B$, and $My_C$, which move during heart contraction along respective paths A, B and C. After an initial period of time, the time between successive image frames in this example, the points in the myocardium have contracted to the positions along paths A, B, and C as shown in FIG. 2B. After the next inter-frame period of time the myocardial points have moved further to the positions shown in FIG. 2C. The continual motion of this movement is now captured by ultrasonic imaging, but only the myocardial point locations at the time an image frame is acquired. Thus, the motion as captured by ultrasound imaging is a succession of straight-line displacements 60 as shown in FIG. 2D. This displacement, when depicted in the larger context of myocardial contraction, would appear as shown in FIG. 3. This drawing shows a short axis view of the myocardium in which the myocardial slice through the heart appears like a donut. At the starting point of the myocardial points in FIG. 2A these points are arrayed as shown at the left side of FIG. 3. After the heart has contracted, the points have moved inward and are closer together as shown on the right side of FIG. 3. In a typical healthy heart, points of myocardial muscle can be expected to move 20% closer together over the contractile phase of the heart. This displacement of each myocardial point is represented by a single value after Lagrangian integration and strain calculation in the ultrasound system. The resulting strain values are then used in the spatially arranged color map of strain values.

In certain aspects, the present invention includes methods of producing real time ultrasonic strain images. The methods can include acquiring frames of echo image data, estimating tissue displacements between acquired frames from the echo image data, calculating strain values from the displacements, forming a color map of the strain values, acquiring additional frames of echo image data, warping the color map to the additional frames, displaying the additional frames in combination with warped color maps generated by warping the color map to the additional frames.

In some aspects, acquiring frames of echo image data can include acquiring image frames of a heart. Estimating tissue displacements can include performing speckle tracking. The speckle tracking can include estimating displacements by cross-correlation, and performing Lagrangian integration of displacements. In certain embodiments, the methods can include acquiring a patient ECG waveform, and acquiring the frames of echo image data in relating to the timing of the ECG waveform.

Warping the color map can include fitting the color map to the boundaries of the myocardium in each of the additional frames. Warping the color map can include fitting the color map to the speckle pattern in each of the additional frames.

Figure 4:
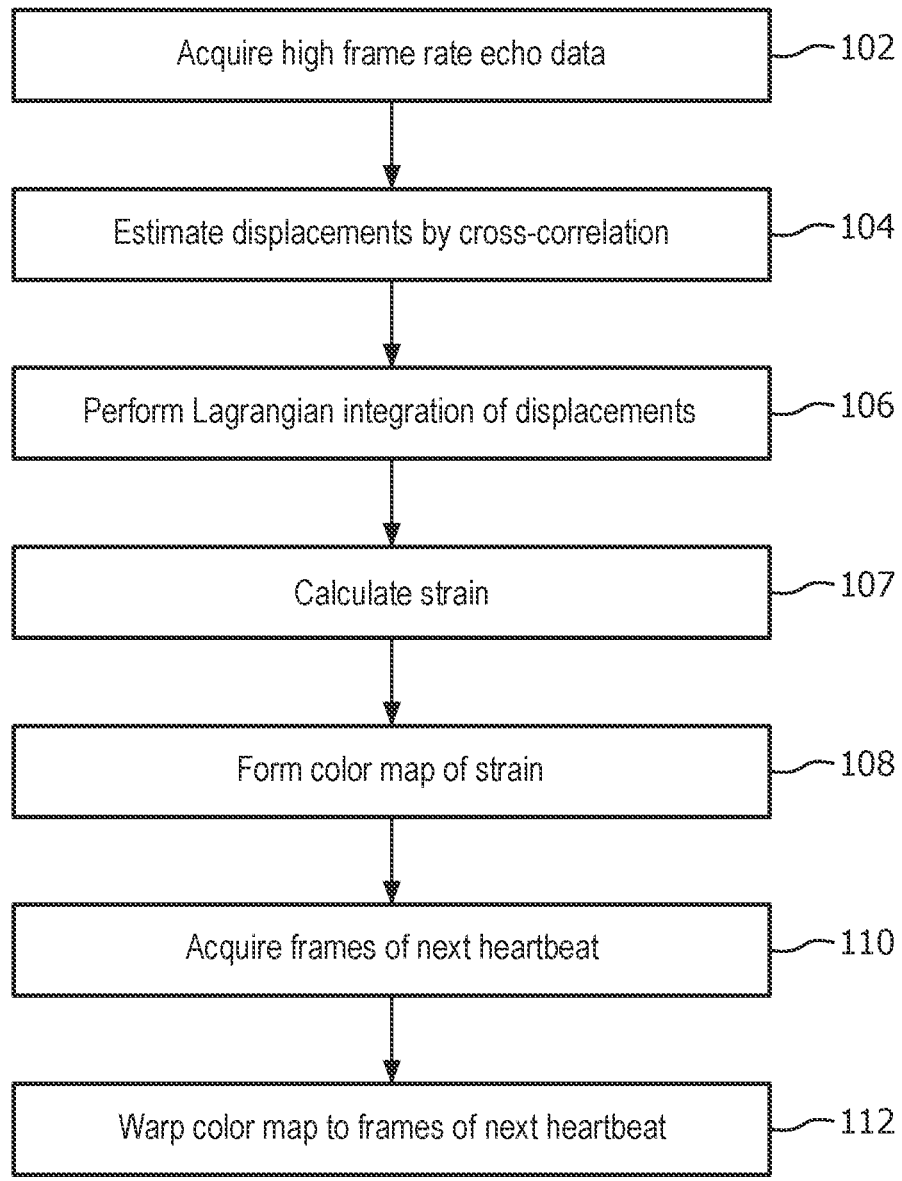
FIG. 4 is a flowchart of strain imaging of the heart in accordance with the principles of the present invention.

The method of the present invention is depicted in the flowchart of FIG. 4. The first step 102 is to acquire high frame rate echo data. The higher the frame rate of the image frames, the smaller the displacement increments of the points in the myocardium (see FIG. 2D)). Preferably image frames are acquired at a rate of 100 Hz or greater. A higher frame rate will provide improved performance when 2D images are used which are subject to movement of myocardial points out of the image plane. The higher frame rate will help assure that a myocardial point is sampled at least two times before it leaves the image plane, enabling a strain estimation to be made for the point. Next, speckle tracking is begun by estimating displacements of features in the image frame such as speckle by cross-correlation at 104. In step 106 Lagrangian integration of the displacements is performed. In step 106 strain is calculated as the spatial derivatives of the displacements. The strain values are then used to form a color map in step 108.

In step 110 image frames of the next heartbeat are acquired. The color map is then warped to fit the myocardium in the image frames of the next heartbeat, and displayed as a color overlay over the myocardium in the new image. The warping and overlay process is continued throughout the next heartbeat while, as the same time, image frames of the next heartbeat are processed to form a color map to be used as a warped overlay with the image frames of the following heart cycle.

It will be understood that each block of the block diagram illustrations, and combinations of blocks in the block diagram illustrations, as well any portion of the systems and methods disclosed herein, can be implemented by computer program instructions. These program instructions may be provided to a processor to produce a machine, such that the instructions, which execute on the processor, create means for implementing the actions specified in the block diagram block or blocks or described for the systems and methods disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable hardware medium including, but not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computing device. Processors can include hardware such as microprocessors, field programmable gate arrays (FPGAs), integrated circuits, or the like.

What is claimed is:

1. An ultrasonic diagnostic imaging system for strain imaging comprising:
   a source of ultrasound echo signals;
   an image processor, coupled to the source of ultrasound echo signals, which is configured to produce a first sequence of image frames over a first heart cycle;
   a processor configured to execute computer program instructions adapted to produce actions of:
      a strain calculator coupled to the image processor and configured to process the image frames to estimate strain values during the first image frame sequence;
      a color mapper configured to produce a color map based at least in-part on the strain values generated by the strain calculator; and
      a color map warper that is responsive to the color map and a new sequence of image frames generated by the image processor during a subsequent heart cycle, wherein the color map warper is configured to warp the color map to fit each of the image frames of the new sequence to generate a plurality of warped color maps; and
   a display configured to display the image frames of the new sequence in real time, each in combination with one of the plurality of warped color maps.

2. The ultrasonic diagnostic imaging system of claim 1, wherein the processor is further configured to execute computer program instructions adapted to produce the action of a displacement estimator responsive to the first or the new sequence of image frames which estimates tissue displacements over each of the image frame sequences.

3. The ultrasonic diagnostic imaging system of claim 2, wherein the computer program instructions, when executed by the processor to produce the action of the displacement estimator further are adapted to produce the action of:
   a displacement cross-correlator which estimates displacement values of the tissue displacements by cross-correlating echo data; and
   a displacement integrator which performs Lagrangian integration on the displacement values.

4. The ultrasonic diagnostic imaging system of claim 3, wherein the computer program instructions when executed by the processor are further adapted to produce the action of a speckle tracker which identifies the tissue displacements.

5. The ultrasonic diagnostic imaging system of claim 4, further comprising an electrocardiograph (ECG) sensor, coupled to the ultrasound system, and configured to sense an ECG waveform.

6. The ultrasonic diagnostic imaging system of claim 5, further comprising a beamformer, coupled to an array transducer, which operates to acquire each of the image frame sequences in relation to the ECG waveform.

7. The ultrasonic diagnostic imaging system of claim 1, wherein the strain calculator is configured to estimate the strain for each pixel of an image frame of the first sequence as a representation of a local strain.

8. The ultrasonic diagnostic imaging system of claim 3, wherein the strain calculator is configured to estimate the strain based on the tissue displacements of image frames of one of the sequences.

9. A computer program product embodied in non-volatile memory, comprising computer-executable instructions for displaying strain values in color maps, executing the steps of:
   acquiring image frames comprising echo image data over a first heart cycle;
   estimating tissue displacements between the acquired frames from the echo image data;
   calculating strain values based at least in-part on the tissue displacements;
   forming a color map of the strain values for the first heart cycle;
   acquiring additional image frames comprising echo image data during a subsequent heart cycle;
   warping the color map to fit each of the additional image frames of the subsequent heart cycle; and
   displaying the additional image frames in real time, each one being displayed in combination with a color map which has been warped to fit that additional image frame.

10. The computer program product of claim 9, wherein estimating tissue displacements further comprises performing speckle tracking.

11. The computer program product of claim 10, wherein speckle tracking further comprises:
    estimating the tissue displacements by cross-correlation; and
    performing Lagrangian integration of the tissue displacements.

12. The computer program product of claim 11, further comprising instructions for executing steps of:
    acquiring a patient electrocardiograph (ECG) waveform; and
    acquiring the image frames comprising echo image data in relating to a timing of the ECG waveform.

13. The computer program product of claim 12, wherein warping the color map further comprises fitting the color map to boundaries of a myocardium in each of the additional frames.

14. The computer program product of claim 12, wherein warping the color map further comprises fitting the color map to a speckle pattern in each of the additional frames.

* * * * *